(12) United States Patent
Clement et al.

(10) Patent No.: US 7,217,270 B2
(45) Date of Patent: May 15, 2007

(54) METHOD AND MATERIAL FOR COATING ELECTRO-CAUTERY PROBES AND LUBRICATING SURGICAL INSTRUMENTS

(75) Inventors: Thomas P. Clement, Bloomington, IN (US); Wayne Miller, Estero, FL (US)

(73) Assignee: Mectra Labs, Inc., Bloomfield, IN (US)

( * ) Notice: Subject to any disclaimer, the term of this patent is extended or adjusted under 35 U.S.C. 154(b) by 381 days.

(21) Appl. No.: 10/776,781

(22) Filed: Feb. 11, 2004

(65) Prior Publication Data

US 2005/0055021 A1 Mar. 10, 2005

Related U.S. Application Data

(60) Provisional application No. 60/501,050, filed on Sep. 8, 2003.

(51) Int. Cl.
*A61B 18/14* (2006.01)
(52) U.S. Cl. .............. 606/45; 606/41; 606/49
(58) Field of Classification Search ............ 606/45, 606/49; 427/2.1, 2.12
See application file for complete search history.

(56) References Cited

U.S. PATENT DOCUMENTS

| | | | |
|---|---|---|---|
| 3,661,605 A | 5/1972 | Rubin et al. | |
| 4,163,676 A | 8/1979 | Konigsbacher | |
| 4,269,174 A * | 5/1981 | Adair | 128/842 |
| 4,314,559 A | 2/1982 | Allen | |
| 4,524,085 A | 6/1985 | Purves et al. | |
| 4,744,992 A * | 5/1988 | Mitchell et al. | 426/29 |
| 4,785,807 A | 11/1988 | Blanch | |
| 5,100,402 A | 3/1992 | Fan | |
| 5,197,962 A | 3/1993 | Sansom et al. | |
| 5,370,732 A | 12/1994 | Follmer | |
| 5,380,320 A | 1/1995 | Morris | |
| 5,498,421 A * | 3/1996 | Grinstaff et al. | 424/450 |
| 5,549,604 A | 8/1996 | Sutcu et al. | |
| 5,618,336 A | 4/1997 | Wagner | |
| 5,643,580 A * | 7/1997 | Subramaniam | 424/400 |
| 5,658,374 A | 8/1997 | Glover | |
| 5,662,956 A | 9/1997 | Knightly | |
| 5,702,387 A | 12/1997 | Arts et al. | |
| 5,713,895 A | 2/1998 | Lontine et al. | |
| 5,782,795 A * | 7/1998 | Bays | 604/22 |
| 5,824,359 A * | 10/1998 | Khan et al. | 427/2.3 |
| 5,897,553 A * | 4/1999 | Mulier et al. | 606/41 |
| 5,900,048 A | 5/1999 | Olson et al. | |

(Continued)

OTHER PUBLICATIONS

Megadyne® (Draper, UT) Brochure/advertisement for the E-Z Clean® electro-cautery tip, 1 page.

(Continued)

*Primary Examiner*—Michael Peffley
*Assistant Examiner*—Alex Toy
(74) *Attorney, Agent, or Firm*—Barnes & Thornburg LLP

(57) ABSTRACT

A coating is provided for use in lubricating an electro-cautery probe of a cauterization device to resist sticking of tissue on the electro-cautery probe. The coating is also provided to lubricate other medical instruments as well as to facilitate sliding of one instrument against another. The coating includes an amphiphilic lipid. The coating also includes an amphiphilic phospholipid, a glycerol-based lipid, a glycerol-based phospholipid, and/or a lecithin.

13 Claims, 2 Drawing Sheets

U.S. PATENT DOCUMENTS

| | | | |
|---|---|---|---|
| 5,921,999 A * | 7/1999 | Dileo | 606/166 |
| 6,015,420 A * | 1/2000 | Wulfman et al. | 606/168 |
| 6,046,143 A | 4/2000 | Khan et al. | |
| 6,066,602 A | 5/2000 | Khan et al. | |
| 6,070,444 A | 6/2000 | Lontine et al. | |
| 6,113,970 A | 9/2000 | Rainey et al. | |
| 6,129,751 A * | 10/2000 | Lucchesi et al. | 607/127 |
| 6,358,248 B1 * | 3/2002 | Mulier et al. | 606/41 |
| 6,405,733 B1 * | 6/2002 | Fogarty et al. | 128/899 |
| 6,447,835 B1 | 9/2002 | Wang et al. | |
| 6,458,867 B1 | 10/2002 | Wang et al. | |
| 6,540,745 B1 | 4/2003 | Fairbourn et al. | |
| 6,589,215 B2 | 7/2003 | Yang et al. | |
| 6,610,035 B2 | 8/2003 | Yang et al. | |
| 6,673,053 B2 | 1/2004 | Wang et al. | |
| 6,443,980 B1 | 9/2006 | Wang et al. | |
| 2002/0010463 A1 * | 1/2002 | Mulier et al. | 606/41 |

OTHER PUBLICATIONS

Riceland Foods, Inc. (Little Rock, Arkansas) Lecithin Division, www.lecithin.com, 84 pages from website, Dec. 8, 2003.

"Experts in electrosurgery," advertisement for EDGE™ coated electrodes sold by Valleylab™, 1 page, © 2002.

* cited by examiner

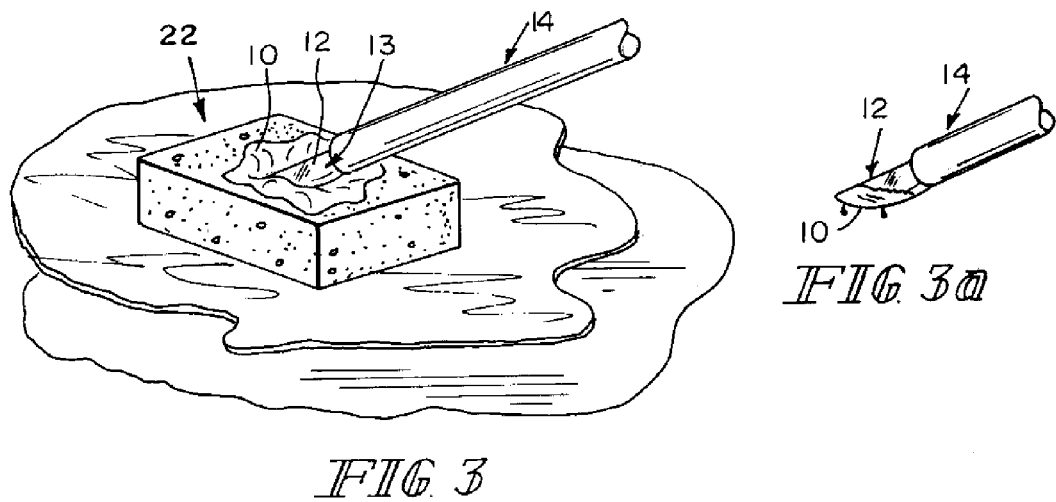
FIG. 3
FIG. 3a
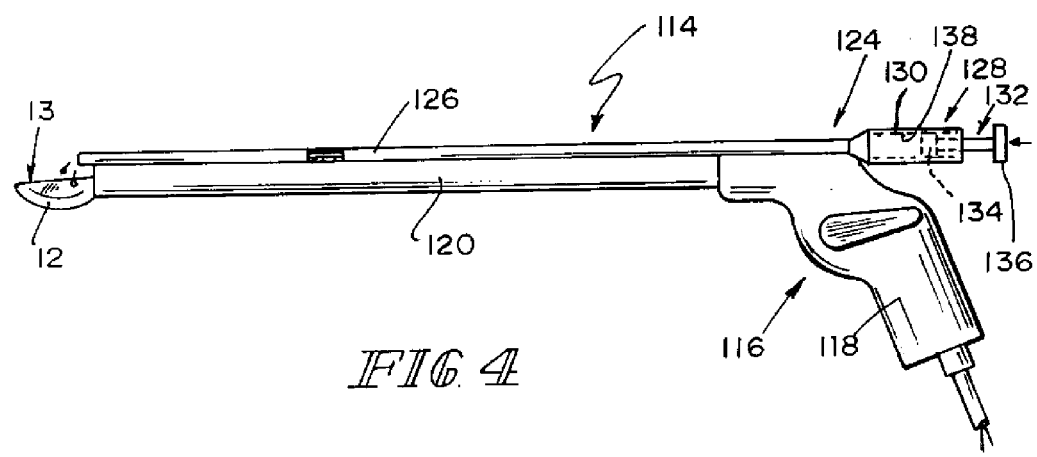
FIG. 4

METHOD AND MATERIAL FOR COATING ELECTRO-CAUTERY PROBES AND LUBRICATING SURGICAL INSTRUMENTS

CROSS-REFERENCE TO RELATED APPLICATION

This application claims priority under 35 U.S.C. 119(e) to U.S. Provisional Application Ser. No. 60/501,050, filed Sep. 8, 2003, the disclosure of which is expressly incorporated by reference herein.

FIELD OF THE DISCLOSURE

The present invention relates to a method and material for coating electro-cautery probes and lubricating surgical instruments.

BACKGROUND

Surgical processes of various types often utilize electro-cautery devices for cutting and/or cauterizing, some of which are mono-polar devices and others of which are bi-polar devices. These devices are well known for use in surgery and can be acquired from various suppliers. Such electro-cautery probes, which are often referred to as "tips," may char and collect tissue fragments on the electro-cautery probes as they are used in surgery. Such charring and accumulation of tissue fragments may degrade the performance of the probes and cause decreased efficiency of the electrodes thus presenting the need to clean or replace the electrodes during cauterization procedures.

The prior art has suggested a variety of man-made or synthetic materials for coating electro-cautery probes. Such prior art includes U.S. Pat. Nos. 4,314,559; 4,785,807; 5,100,402; 5,197,962; 5,380,320; 5,549,604; 5,702,387; 5,713,895; 6,070,444; and 6,540,745, for example. The disclosure of each of these references is hereby incorporated by reference herein. Further, Megadyne® (headquartered in Draper, Utah) provides the E-Z Clean® electro-cautery tip which is advertised as being a non-stick electro-cautery tip or probe which reduces eschar, or scabbed tissue, buildup.

Also, in surgery procedures involving inserting instruments into other instruments, there is a need for lubrication of the instruments.

SUMMARY

The present disclosure comprises one or more of the following features or elements or the combination thereof:

A coating is provided for electro-cautery probes to reduce the charring and accumulation of tissue fragments thereon when such probes are used in surgery. The coating, which is applied to the probes, is effective for preventing such sticking of tissue. The coating is also effective as a lubricant for use in surgery to facilitate movement of instruments relative to each other. For example, the coating may be used to facilitate insertion of instruments into trocars in laparoscopic surgery. Illustratively, the coating is provided in a liquid form.

The illustrative coating includes an amphiphilic lipid and more specifically may include an amphiphilic phospholipid, a glycerol-based lipid, a glycerol-based phospholipid, and/or a lecithin. The lecithin of the coating is a non-allergenic lecithin from which a soy protein component is removed to make the coating non-allergenic.

The coating may illustratively be applied to the electro-cautery probes by dipping the probes in or wiping the probes with the coating. For example, a method for coating electro-cautery probes in a surgery procedure in an operating room includes providing a cauterization device having at least one electro-cautery probe to cut and/or cauterize tissue, providing a container of liquid coating for lubricating the at least one electro-cautery probe, and applying the liquid coating in the container to a tip of the electro-cautery probe. The illustrative cauterization device, and all cauterization devices disclosed herein may be bi-polar or mono-polar cauterization devices.

Further, a kit may be provided for lubricating an electro-cautery probe of a cauterization device. The kit may include the above-discussed coating, a container containing the coating, and a sterile pad having a top surface formed to receive a portion of the coating. The pad may include a foam portion, an adhesive provided on at least one surface of the foam portion, and a removable backing coupled to the adhesive.

In a presently preferred aspect of the invention, the coating is supplied as a liquid for use by surgeons or technicians directly in the operating room to coat the electro-cautery probes before and during surgery without any heating or curing. Small containers of a lecithin coating may be supplied with sterile pads for applying the coating to the probes. Further, a surgeon, technician, or other user may attach the pad of the kit to an area adjacent a cauterization site prior to the cauterization procedure and may place a portion of the coating onto a top surface of the pad. The user may then dip the tip of the electro-cautery probe into the coating provided on the top surface of the pad prior to cauterizing a patient's tissue. The user may re-dip the tip of the electro-cautery probe into the coating as often as desired or necessary throughout the cauterization process.

In another embodiment, the cauterization device of the present disclosure may include a mechanism for dispensing the lubricating coating onto the tip of the electro-cautery probe of the cauterization device. The illustrative lubricating mechanism is coupled to a main body of the cauterization device and includes a hollow tube forming a channel positioned along an insulator of the main body of the cauterization device. A syringe portion of the lubrication mechanism is coupled to a proximal end of the hollow tube to be positioned near a gripping handle of the main body.

The syringe portion includes a receptacle coupled to the insulator of the main body. The receptacle defines a cavity configured to receive the coating therein. The syringe portion further includes a plunger having a sealed stopper end positioned within the cavity of the receptacle and a handle coupled to the plunger for a user to grip. The plunger is movable back and forth within the cavity relative to the receptacle in order to move the coating within the receptacle into the insulator and onto the tip of the electro-cautery probe.

A method, therefore, of lubricating an electro-cautery probe of the cauterization device includes providing the coating within a lubrication dispensing mechanism coupled to an insulator of the cauterization device and dispensing the coating onto a tip of the electro-cautery probe. The user may depress the plunger of the syringe portion to advance the coating contained within the syringe portion through the lubricating mechanism and onto the tip of the electro-cautery probe.

The same coating discussed above for coating electro-cautery probes may also be supplied to surgeons or technicians for use in lubricating the blades of bipolar scissors, for example, as well as lubricating surgical instruments or portions of instruments to facilitate movement of the instruments relative to each other in surgical applications.

Features of the present disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The detailed description particularly refers to the accompanying figures in which:

FIG. 3 is a perspective view showing the tip of the electro-cautery probe being dipped into the lecithin solution which was poured onto the foam block;

FIG. 3a is a perspective view showing the tip of the electro-cautery probe coated with the lecithin solution; and FIG. 4 is a side view of an alternative cauterization device of the present disclosure showing a lubricating mechanism of the alternative cauterization device provided to allow a user to continuously, or as needed, lubricate the tip of the electro-cautery probe without the need, for example, to re-dip the electro-cautery probe into a solution.

DETAILED DESCRIPTION OF THE DRAWINGS

Figure 2:
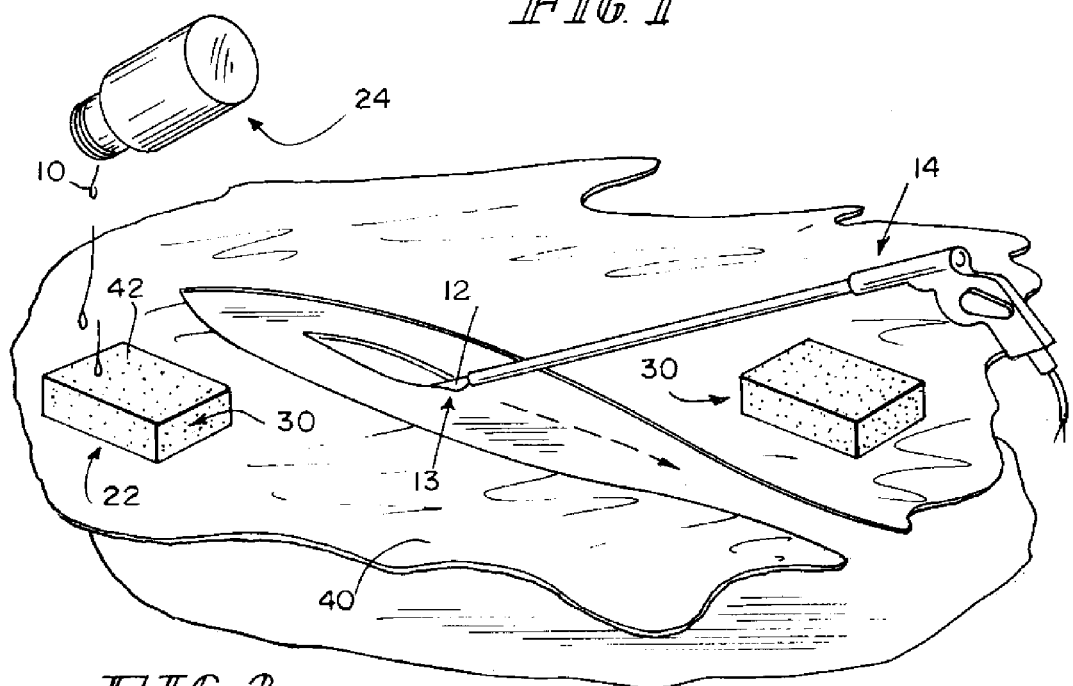
FIG. 2 is a perspective view of the components of the kit and cauterization device in use during surgery showing one of the foam blocks of the kit adhered to the drape and showing the lecithin solution being poured onto the foam block such that a tip of an electro-cautery probe of the cauterization device may be dipped as needed into the lecithin solution during the cauterization process in order to substantially prevent tissue fragments from collecting the tip of the electro-cautery probe.

A non-stick, liquid coating 10 is provided for coating a tip 12 of an electro-cautery probe 13 of an illustrative cauterization device 14 in order to prevent tissue fragments from sticking to and coating tip 12 of cauterization device 14 during a cut and/or cauterization procedure, such as that shown in FIG. 2, for example. The term cauterization procedure herein refers to any type of surgical cut and/or cauterization-type procedure. Illustratively, coating 10 is effective for preventing such sticking or accumulation of tissue and may also be effective as a lubricant for use in other surgeries to facilitate movement of instruments relative to each other. For example, the coating 10 may be used to facilitate insertion of instruments into trocars in laparoscopic surgery.

Illustrative coating 10 is made from a natural or biological material which is safe to use during surgery. In one embodiment, the coating 10 comprises an amphiphilic lipid. As used herein, the term "amphiphilic" refers to a property where a molecule has both a polar portion and a non-polar portion. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt.

Without being bound by theory, it is postulated that amphiphilic lipids are particularly suited for use as coatings of electro-cautery probes due to their stabilizing nature. Amphiphilic lipids are able to stabilize both positive and negative sites contained or located on the metallic surface or tip, such as tip 12, of the electro-cautery probe 13 of a cauterization device, such as device 14, for example.

Lecithin is an amphiphilic lipid and as such, forms a phospholipids bilayer having thehydrophilic (polar) heads facing their surroundings, which are oftentimes aqueous, and the hydrophobic tails facing each other. This structure allows lecithin to acts as an emulsifier and is, at least in part, what provides lecithin with the non-stick property. Although lecithin is disclosed herein, it is within the scope of this disclosure for coating 10 to include any amphiphilic lipid found to be biocompatible or safe and non-toxic to permit use on patients with cauterization devices or other surgical instruments.

Traditional materials used to coat the surface or tip of cauterization devices are often "man-made" and include fluorocarbons, fluorosilicates, fluorinated hydrocarbon, polytetrafluorethylen (Teflon), parylene, amorphous silica, silicone, fluorinated polymer, other fluorine based resins and fluorinated carbons, and aromatic polycarbons. The coating 10 of the present disclosure, however, is made in whole or in part from natural materials rather than man-made materials. Illustrative coating 10 of the present disclosure, for example, comprises a lecithin. Lecithin compositions are available having a variety of viscosities, such as the commercially available lecithins of Riceland Foods, Inc (Little Rock, Ark.). Specifically, Riceland Foods, Inc. produces a fluid lecithin product line including a full range of lecithin products which are applicable as the coating 10 disclosed herein.

A typical composition of the fluid lecithin products produced by Riceland Foods, Inc. includes 62% acetone insolubles, 37.5% soybean oil, 0.5% moisture, and 0.03% hexane insolubles. A proximate composition of the fluid lecithin products produced by Riceland Foods, Inc. is 90% lipids, 5% carbohydrates, 4.5% ash, and 0.5% moisture. The majority of the lecithin, therefore, is comprised of lipids. Further illustratively, due to the fact that some patients may be allergic to soy products, any and/or all of a soy protein which may be contained within a coating 10 comprising lecithin may be removed in order to provide a non-allergenic lecithin coating. Illustratively, the products LECISOY N-2, LECIPRIME S, and LECIPRIME-N are each suitable for use as coating 10, for example. Each of these products are provided by Riceland Foods.

As used herein, the term lecithin includes any phosaphatidylcholine derivatives of glycerol, and having the general structure depicted by Formula I:

Formula I

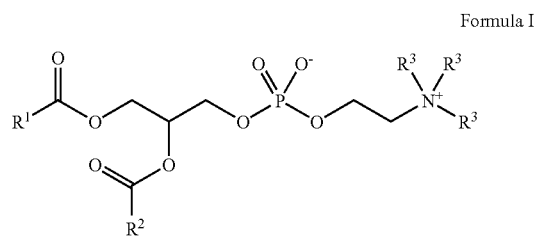

wherein $R^1$ and $R^2$ are each independently selected from alkyl, alkenyl, arylalkyl, and arylalkenyl, each of which may be optionally substituted, and including $C_1$–$C_{30}$ alkyl and $C_1$–$C_{30}$ alkenyl, such as but not limited to stearic, palimitic, oleic, palmitoleic, linoleic, linolenic, and arachidonic acid side chains; and $R^3$ is in each instance independently selected from $C_1$–$C_4$ alkyl, including methyl and ethyl.

It is appreciated that the chiral center in Formula I may be of either stereoconfiguration, or alternatively, a mixture of stereoisomers may be present. Such a mixture of stereoisomers may have an equal population of each stereoisomer, as in a racemic mixture, or may have an unequal population of each stereoisomer, and thus exhibit optical activity.

It is also appreciated that coating components for use as lubricants for electro-cautery probes may be advantageously selected from those components that are stable to higher temperatures, such as those higher temperatures which may be observed on the surface of electro-cautery probes when in use, for example.

Formulations of the coating compositions described herein may also include one or more other components such as alcohols, fatty acids, oils, surfactants, water, dispersing agents, and thixotropic agents. Dispersing agents include, but are not limited to, propylene glycol based ethers, propylene glycol based ether acetates, ethylene glycol based ethers, ethylene glycol based ether acetates, and mixtures thereof.

Lecithin coating 10 may have various properties including differing viscosities, benzene insolubility, acetone insolubility, moisture content, and peroxide value. For example, lecithin may be obtained having different viscosities such as 8090 and 12000 as purchased from Riceland Foods, Inc. Experiments with lecithin coatings having different combinations of these properties have all shown to be effective in preventing charring and/or accumulation of tissue onto the tip of the electro-cautery probe. Therefore, it is within the scope of this disclosure for coating 10 to include all lecithin compositions having any suitable combination of properties described above.

Various lecithins are known to be used as non-stick coatings or release agents to prevent sticking for example of one part to another. Lecithins are often used as release agents in the baking industry for coating baking pans, for example, in the molding industry for coating tire molds, for example, and as spray-on release agents for use on frying pans, for example, when cooking. Such prior art disclosing the use of lecithin as a release agent includes U.S. Pat. Nos. 3,661,605; 4,163,676, 4,524,085; 5,370,732; 5,618,336; 5,658,374; 5,662,956; 5,900,048; and 6,113,970, for example. The disclosure of each of these references is hereby incorporated by reference herein. While such prior uses of lecithin for baking or molding are known, it will be appreciated that in mono-polar and bi-polar cauterizing, the cauterizing is mostly done by RF or high frequency energy and any heating of the probe is a by-product of the process.

Illustratively, as mentioned above, coating 10 is provided to coat tip 12 of the electro-cautery probe or probes 13 of cauterization device 14. Examples of other similar cauterization probes are shown in U.S. Pat. Nos. 1,813,902 and 4,562,838. Cauterization device 14 may include bi-polar electro-cautery probes or mono-polar electro-cautery probes. Coating 10 may be used to coat the tips 12 of either bi-polar or mono-polar probes. Looking now to FIG. 1, a probe-coating kit 20 is provided including two foam blocks or pads 22 and a bottle or container 24 including the liquid, non-stick coating 10 discussed above. Although foam blocks or pads 22 are made of foam, it is within the scope of the disclosure for the pads 22 to made of other suitable materials such as cotton, for example.

Illustratively, an instruction sheet 26 providing instructions for use of the foam blocks 22 and coating 10, as described below, is also provided. The foam blocks 22, bottle 24, and instruction sheet 26 are placed within a clear, plastic pouch 28, sealed, and sterilized prior to use by a surgeon or technician, for example, during surgery or other cauterization process. It is also within this disclosure for foam blocks 22, bottle 24, and instruction sheet 26 to be carried within another suitable container which may be sterilized prior to use by a surgeon or technician.

Each illustrative foam block 22 has a surface area of approximately two inches by two inches and includes a foam portion 30, a removable backing 32, and an adhesive 34 provided on a bottom surface 36 of the foam portion 30. When the foam block 22 is not in use, the removable backing 32 is coupled to the bottom surface 36 of the foam square in order to cover the adhesive 34.

Figure 1:
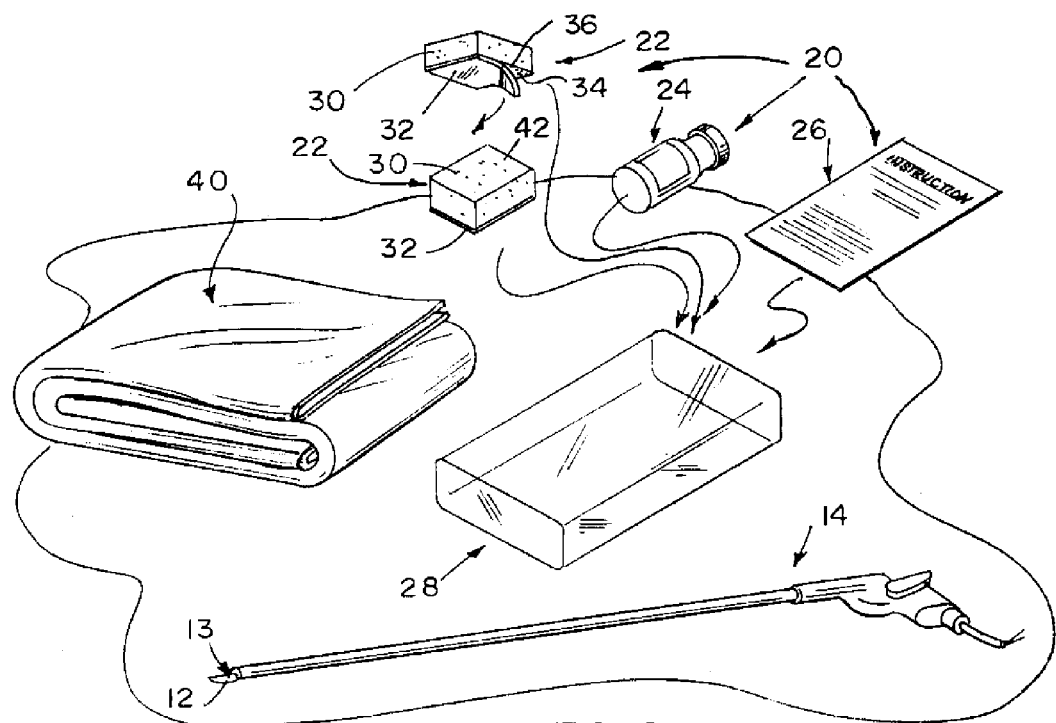
FIG. 1 is a perspective view of a probe-coating kit showing two foam blocks or pads, a bottle containing a non-stick, liquid lecithin solution, and an instruction pamphlet and also showing a cauterization device and a surgical drape for use during various surgical procedures such as cauterization, for example.

In using kit 20, a doctor, technician, or other user opens the plastic pouch 28 and removes the contents (foam blocks 22, bottle 24 containing coating 10, and instruction sheet 26). Backing 32 of one or both of the foam blocks 22 is then removed to expose the adhesive 34 thereon, as shown in FIG. 1, for example. By placing the adhesive-side or bottom surface 36 down, foam portion 30 of foam block 22 may then be coupled onto an outer surface of a patient drape 40, for example, such as that shown in FIG. 2. Foam portion 30 may be adhered to other convenient surfaces near the location where the cauterization is to take place as well, for example. A top surface 42 of foam block 22 provides a surface for placing and holding a desired amount of coating 10. Although foam blocks 22 are provided with kit 20, it is within the scope of this disclosure to include other devices for providing a suitable portable, sterile surface upon which a portion of coating 10 may be conveniently held during the cauterization process such as a small tray, for example.

Thus, once one or both of the foam blocks 22 have been secured to drape 40 or another nearby area, the user opens the bottle 24 containing coating 10 and pours a desired amount of coating 10 onto top surface 42 of foam block 22, as shown in FIG. 2 in order to provide a readily-accessible amount of coating 10 within the vicinity of the area in which the cauterization device 14 is to be used. Further, foam blocks 22 provide a relatively flat and absorbent upper surface 42 to contain or hold the coating 10. As mentioned above, another device or apparatus may be used other than foam blocks 22 to conveniently contain or hold a portion of coating 10 contained within bottle 24 thereon. Further, the device used may be absorbent, such as foam block 22, to contain and hold the coating 10. The surface-providing device may also be made of a material which is not absorbent as well.

As shown in FIGS. 3 and 3a, the tip 12 of the electro-cautery probe 13 of cauterization device 14 is dipped into the coating 10 located on foam square 22 in order to coat a portion of electro-cautery probe tip 12. The user may re-coat tip 12 as often as necessary by dipping tip 12 into coating 10 provided on foam square 22. If additional coating 10 is needed during the procedure, the user may pour additional coating 10 onto the foam square 22. Such a procedure or method of coating the electro-cautery probe tip 12 prevents the surgeon or other user from having to balance the bottle 24 containing the liquid coating 10 near the cauterization site in order to minimize the chances of spilling the bottle 24, for example. Further, such a procedure of coating electro-cautery probe tip 12 including the step of pouring a portion of the coating 10 contained within bottle 26 onto foam square 22 prevents the surgeon or other user from dipping and re-dipping the probe tip 12 into the bottle 26. This allows the coating 10 which remains within the bottle 26 to remain sterile and usable for future procedures. The surgeon or technician may also use the pad 22 to wipe coating 10 onto tip 12 in addition to using the pad 22, as discussed above, to hold or contain coating 10 for dipping of the tip 12 therein.

Therefore, a means or method of coating a electro-cautery probe tip 12 is provided. This method includes dipping or wiping the electro-cautery probe tip 12 into coating 10. More specifically, this method includes placing or adhering one or more portable, sterile surfaces, such as surface 42 of foam blocks 22, onto surgical drape 40, or another convenient area and dispensing a desired amount of coating 10 onto the portable surface 42. The method next includes dipping the electrode tip 12 onto the foam surface containing coating 10. The dipping step may be repeated as often as desired or necessary.

As mentioned above, instruction sheet 26 is also provided in kit 20 and contained within plastic pouch 28. Instruction sheet 26 includes instructions to inform the surgeon or technician how to properly use the contents of kit 20 to coat the tip 12 of cauterization device 14 with the coating 10 contained within bottle or container 24. Illustratively, the instructions on the instruction sheet 26 may read as follows:

1. Place contents of pouch onto sterile field.
2. Remove backing from foam and stick adhesive side down onto patient drape.
3. Remove cap from bottle and dispense desired amount of release coating onto foam.
4. Wipe electrode tip onto foam containing release coating.
5. Repeat as frequently as desired.

Looking now to FIG. 4, an alternative cauterization device 114 is provided. Alternative cauterization device 114 includes a main body 116 having a handle 118 for a user to grip and a long, insulator 120 coupled to handle 118. A tip 12 of the electro-cautery probe 13 of the device 114 is provided at a distal end of insulator 120.

Alternative cauterization device 114 further includes a dispensing mechanism 124 for wetting or lubricating probe tip 12. Dispensing mechanism 124 is coupled to main body 116 and includes a hollow tube or channel 126 positioned along insulator 120 and an actuator 128 coupled to a proximal end of hollow tube 126 to be positioned near handle 118 of main body 116. Illustrative actuator 128 is a syringe-type actuator and includes a receptacle 130 coupled to insulator 120 and forming a cavity for receiving coating 10 therein. A plunger 132 of actuator 128 includes a sealed stopper end 134 positioned within the cavity of the receptacle 130 and a handle 136 for a user to grip. Plunger 132 is movable back and forth within cavity 138 relative to receptacle 130. The actuator of the dispensing mechanism may also be a compressible rubber bulb (not shown) used to inject coating 10 into hollow tube 126.

In use, a desired amount of coating 10 is dispensed into the cavity 138 of the actuator 128 to generally fill the cavity 138 and a portion or all of the hollow tube 126. During use of the cauterization device 114, a user may depress the handle 136 of the plunger 132 to move the plunger 132 to the left, as shown in FIG. 4, in order to dispense an amount of coating 10 out of a distal end of insulator 120 and onto electro-cautery probe tip 12. The surgeon or other user may dispense as much or as little coating 10 onto tip 12 as is desired or necessary to prevent the tip 12 from collecting tissue material as the cauterization device 114 is being used.

Thus, a second means or method for coating an electro-cautery probe tip 12 is provided. This second method includes placing an amount of coating 10 within a dispensing mechanism of a electro-cautery probe, such as dispensing mechanism 124, and dispensing the coating 10 onto the tip 12 of the cauterization device 114 by depressing a plunger 132 of a syringe 128 of the lubricating mechanism 124 as the cauterization device 114 is being used. This second method allows the surgeon or other user to dispense continually, or as needed, the coating 10 onto the electro-cautery probe tip 12 without the need to stop the cauterization procedure and remove the cauterization device 114 from the patient in order to re-lubricate or reapply the coating 10 to tip 12. In other words, coating 10 may be applied throughout the cauterization process. It will be appreciated that, while a syringe-type of mechanism is shown for dispensing coating 10, various types of dispensing mechanism may be coupled to, carried by, or used with a cauterization device to dispense coating onto the probe as required.

As discussed above, kit 20 is provided for allowing a user to dip tip 12 of cauterization device 14 into coating 10 to coat tip 12. Further, alternative cauterization device 114 is provided having lubrication mechanism 124 for dispensing coating 10 onto tip 12 during the cauterization procedure. It is also within the scope of this disclosure, however, to dispense coating 10 from a spray bottle (not shown) onto tip 12. For example, a user may simple spray tip 12 with the coating 10 contained within the spray bottle prior to the cauterization procedure. The spray bottle may be either a pump or a gas driven spray bottle.

Although release coating 10 is described above for use with cauterization devices 14, 114 having electro-cautery probes 13, it is understood that the term cauterization device includes other suitable devices used in cauterization-type processes, such as bipolar scissors (not shown), for example, in order to prevent charring or accumulation of tissue onto the device. Illustrative release coating 10 may be used to coat the scissor blades (not shown) of a bipolar scissors in the manner discussed above with respect to devices 14, 114. Other surgical devices may also be lubricated or coated with coating 10. Coating 10 may be used to lubricate various surgical instruments to facilitate movement of the instruments relative to each other during use. For example, coating 10 may be used to facilitate insertion of instruments into trocars in laparoscopic surgery.

The invention claimed is:

1. An electro-cautery probe not designed for penetrating the skin prior to electro-cauterization and for attachment to and use with a cauterization device to cut and/or cauterize tissue of a patient in surgery, the electro-cautery probe having at least a surface of the electro-cautery probe which contacts a patient's tissue to be cut and/or cauterized coated with a coating comprising an amphiphilic lipid.

2. The electro-cautery probe of claim 1, wherein the coating comprises an amphiphilic phospholipid.

3. The electro-cautery probe of claim 1, wherein the coating comprises a glycerol-based lipid.

4. The electro-cautery probe of claim 1, wherein the coating comprises a glycerol-based phospholipid.

5. The electro-cautery probe of claim 1, wherein the coating comprises a lecithin.

6. The electro-cautery probe of claim 5, wherein the lecithin is a non-allergenic lecithin.

7. The electro-cautery probe of claim 5, wherein the lecithin is of 8090 viscosity.

8. The electro-cautery probe of claim 5, wherein the lecithin is of 12000 viscosity.

9. The electro-cautery probe of claim 5, wherein the lecithin is a lecithin from which a soy protein component is removed to make the coating non-allergenic.

10. The electro-cautery probe of claim 5, wherein the release coating comprises a compound having the formula:

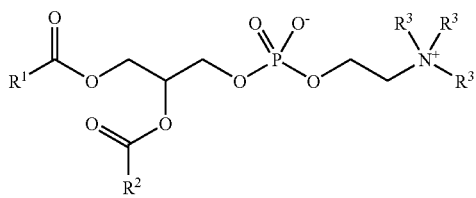

wherein $R^1$ and $R^2$ are each independently selected from alkyl and alkenyl, each of which may be optionally substituted; and $R^3$ is in each instance independently selected from $C_1$–$C_4$ alkyl.

11. A cauterization device comprising
an electro-cautery probe tip not designed for penetrating the skin prior to electro-cauterization and having a surface area which contacts a patient's tissue to be cauterized, and liquid means for preventing the patient's tissue from sticking to the electro-cautery probe tip wherein the liquid means for preventing the patient's tissue from sticking to the electro-cautery probe tip includes a coating comprising an amphiphilic lipid.

12. The cauterization device of claim 11, wherein the liquid means for preventing the patient's tissue from sticking to the electrocautery probe tip includes means for continually dispensing the coating onto the electro-cautery probe tip during cauterization.

13. The cauterization device of claim 11, wherein the liquid means for preventing the patient's tissue from sticking to the electro-cautery probe tip includes means for dispensing the coating onto the electro-cautery probe tip during cauterization as needed without the need to stop the cauterization procedure and without removing the probe tip from the patient.

* * * * *